(12) United States Patent
Pavlik (10) Patent No.: US 10,123,940 B2
(45) Date of Patent: *Nov. 13, 2018

(54) BAG ASSEMBLY AND SYSTEM FOR USE WITH A FLUID

(71) Applicant: ADVANCED SCIENTIFICS, INC., Millersburg, PA (US)

(72) Inventor: Rudolf Pavlik, Millersburg, PA (US)

(73) Assignee: Advanced Scientific, Inc., Millersburg, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/953,227

(22) Filed: Apr. 13, 2018

(65) Prior Publication Data

US 2018/0228694 A1    Aug. 16, 2018

Related U.S. Application Data

(63) Continuation of application No. 14/738,442, filed on Jun. 12, 2015, now Pat. No. 9,968,519, which is a continuation of application No. 14/315,936, filed on Jun. 26, 2014, now Pat. No. 9,079,690.

(51) Int. Cl.
| | |
|---|---|
| *A61J 1/16* | (2006.01) |
| *A01N 1/02* | (2006.01) |
| *B65D 30/16* | (2006.01) |
| *F25D 31/00* | (2006.01) |

(Continued)

(52) U.S. Cl.
CPC .............. *A61J 1/16* (2013.01); *A01N 1/0263* (2013.01); *A01N 1/0268* (2013.01); *A61J 1/10* (2013.01); *A61J 1/1475* (2013.01); *B65D 31/06* (2013.01); *F25D 31/00* (2013.01)

(58) Field of Classification Search
CPC ......... A61J 1/16; A61J 1/1475; A01N 1/0263; A01N 1/0268; B65D 31/06; F25D 31/00; B60R 21/233; B60R 21/231; B60R 21/207; A61M 1/001

See application file for complete search history.

(56) References Cited

U.S. PATENT DOCUMENTS

| | | |
|---|---|---|
| 1,269,189 A | 6/1918 | Kadish |
| 1,471,332 A | 10/1923 | Greenawalt |
| 1,505,204 A | 8/1924 | Kiernan |

(Continued)

FOREIGN PATENT DOCUMENTS

| | | |
|---|---|---|
| CA | 2214384 | 10/1996 |
| CH | 675368 A5 | 9/1990 |

(Continued)

OTHER PUBLICATIONS

DuPont Medical Packaging, Technical Reference Guide for Medical Packaging, The Miracles of Science, 2002.

*Primary Examiner* — Emmanuel Duke
(74) *Attorney, Agent, or Firm* — Workman Nydegger (57) ABSTRACT

A bag assembly includes a pliable housing having a first panel secured to a second panel by a seam so that a cavity is formed between the first panel and the second panel, the seam encircling the cavity. A first tufting couples together the first panel and the second panel at a location spaced apart from the seam so that the cavity encircles the first tufting. In one embodiment the first tufting can circular. A first port is coupled with the pliable housing and communicating with the cavity.

20 Claims, 4 Drawing Sheets

(51) Int. Cl.
*A61J 1/14* (2006.01)
*A61J 1/10* (2006.01)

(56) References Cited

U.S. PATENT DOCUMENTS

| | | | |
|---|---|---|---|
| 2,259,243 A | 10/1941 | Daman | |
| 2,341,114 A | 2/1944 | Novak | |
| 2,865,618 A | 12/1958 | Abell | |
| 3,074,544 A * | 1/1963 | Bollmeier | B29C 65/76 206/219 |
| 3,184,395 A | 5/1965 | Brewer | |
| 3,207,420 A | 9/1965 | Navarrete-Kindelan | |
| 3,608,709 A * | 9/1971 | Pike | B29C 65/76 206/219 |
| 3,647,397 A | 3/1972 | Coleman | |
| 3,682,168 A | 8/1972 | Deaton | |
| 3,701,433 A | 10/1972 | Krakauer | |
| 3,702,619 A | 11/1972 | Son | |
| 3,796,417 A | 3/1974 | Kaelin | |
| 4,012,471 A | 3/1977 | Kunkle, Jr. | |
| 4,012,473 A | 3/1977 | Lindsey et al. | |
| 4,025,590 A | 5/1977 | Igich | |
| 4,036,919 A | 7/1977 | Komendowski et al. | |
| 4,061,698 A | 12/1977 | Thornwald | |
| 4,100,235 A | 7/1978 | Thornwald | |
| 4,157,965 A | 6/1979 | Raible | |
| 4,204,774 A | 5/1980 | de Bruyne | |
| 4,250,039 A | 2/1981 | Cozzi et al. | |
| 4,391,912 A | 7/1983 | Yoshida | |
| 4,402,402 A * | 9/1983 | Pike | B65D 81/3266 206/219 |
| 4,458,811 A | 7/1984 | Wilkinson | |
| 4,465,645 A | 8/1984 | Kaelin | |
| 4,493,637 A | 1/1985 | Ganter et al. | |
| 4,581,143 A | 4/1986 | Pepper | |
| 4,668,632 A | 5/1987 | Young et al. | |
| 4,684,486 A | 8/1987 | Ricchio | |
| 4,727,040 A | 2/1988 | Freedman et al. | |
| 4,740,202 A | 2/1988 | Stacey et al. | |
| 4,749,654 A | 6/1988 | Karrer et al. | |
| 4,814,124 A | 3/1989 | Aoyama et al. | |
| 4,869,398 A | 9/1989 | Colvin | |
| 4,869,852 A | 9/1989 | Goudy, Jr. et al. | |
| 4,981,623 A | 1/1991 | Ryan | |
| 5,008,197 A | 4/1991 | Wergeland et al. | |
| 5,057,429 A | 10/1991 | Watanabe et al. | |
| 5,139,946 A | 8/1992 | Howell et al. | |
| 5,183,595 A | 2/1993 | Schüssler | |
| RE34,386 E | 9/1993 | Davidson et al. | |
| 5,270,207 A | 12/1993 | Matsumura et al. | |
| 5,287,961 A * | 2/1994 | Herran | B65D 81/3266 206/219 |
| 5,376,271 A | 12/1994 | Morgan, Jr. | |
| 5,416,022 A | 5/1995 | Amiot | |
| 5,422,043 A | 6/1995 | Burris | |
| 5,431,496 A | 7/1995 | Balteau | |
| 5,443,985 A | 8/1995 | Lu et al. | |
| 5,458,771 A | 10/1995 | Todd | |
| 5,487,470 A | 1/1996 | Pharo | |
| 5,547,108 A | 8/1996 | Gsell | |
| 5,565,015 A | 10/1996 | Kobayashi | |
| 5,578,459 A | 11/1996 | Gordon | |
| 5,693,537 A | 12/1997 | Wilson et al. | |
| 5,714,384 A | 2/1998 | Wilson et al. | |
| 5,763,267 A | 6/1998 | Kurjan | |
| 5,788,661 A | 8/1998 | Japuntich | |
| 5,799,830 A | 9/1998 | Carroll et al. | |
| 5,858,015 A | 1/1999 | Fini | |
| 5,858,283 A | 1/1999 | Burris | |
| 5,897,997 A | 4/1999 | Louvel | |
| 5,925,293 A | 7/1999 | Howk | |
| 5,941,635 A | 8/1999 | Stewart | |
| 6,017,598 A * | 1/2000 | Kreischer | A61J 1/10 428/35.4 |
| 6,068,775 A | 5/2000 | Custer et al. | |
| 6,071,005 A | 6/2000 | Ekambaram et al. | |
| 6,083,587 A | 7/2000 | Smith et al. | |
| 6,086,574 A | 7/2000 | Carroll et al. | |
| 6,099,734 A | 8/2000 | Boggs | |
| 6,117,801 A | 9/2000 | McGinty et al. | |
| 6,146,875 A | 11/2000 | Ward | |
| 6,186,932 B1 | 2/2001 | Vallot | |
| 6,219,871 B1 | 4/2001 | Frederick et al. | |
| 6,245,555 B1 | 6/2001 | Curtis | |
| 6,250,796 B1 | 6/2001 | Huang | |
| 6,251,295 B1 | 6/2001 | Johnson | |
| H1989 H | 9/2001 | Fell et al. | |
| 6,367,783 B1 | 4/2002 | Raftis | |
| 6,391,638 B1 | 5/2002 | Shaaltiel | |
| 6,398,195 B1 | 6/2002 | Sherman | |
| 6,406,005 B1 | 6/2002 | Lawson et al. | |
| 6,432,698 B1 | 8/2002 | Gaugler et al. | |
| 6,439,756 B1 | 8/2002 | Forschner et al. | |
| 6,464,211 B1 | 10/2002 | Downs | |
| 6,468,792 B1 | 10/2002 | Bader | |
| 6,494,613 B2 | 12/2002 | Terentiev | |
| 6,518,057 B2 | 2/2003 | Morrison | |
| 6,596,521 B1 | 7/2003 | Chang et al. | |
| 6,632,658 B1 | 10/2003 | Schoeb | |
| 6,642,019 B1 | 11/2003 | Anderson et al. | |
| 6,649,405 B2 | 11/2003 | Alms et al. | |
| 6,670,169 B1 | 12/2003 | Schöb et al. | |
| 6,673,598 B1 | 1/2004 | Akers et al. | |
| 6,709,862 B2 | 3/2004 | Curtis | |
| 6,712,963 B2 | 3/2004 | Schick | |
| 6,745,902 B2 | 6/2004 | Lunn et al. | |
| 6,884,866 B2 | 4/2005 | Bronshtein et al. | |
| 6,908,223 B2 | 6/2005 | Bibbo et al. | |
| 6,923,567 B2 | 8/2005 | Bibbo et al. | |
| 6,969,367 B2 | 11/2005 | Hosheng | |
| 7,141,203 B2 | 11/2006 | Way et al. | |
| 7,198,225 B2 | 4/2007 | Chiba | |
| 7,278,780 B2 | 10/2007 | Goodwin et al. | |
| 7,326,355 B2 | 2/2008 | Graetz et al. | |
| 7,384,027 B2 | 6/2008 | Terentiev et al. | |
| 7,384,783 B2 | 6/2008 | Kunas et al. | |
| 7,390,652 B2 | 6/2008 | Condon et al. | |
| 7,431,837 B2 | 10/2008 | Cohee et al. | |
| 7,448,601 B2 | 11/2008 | Boer | |
| 7,469,884 B2 | 12/2008 | Terentiev et al. | |
| 7,629,167 B2 | 12/2009 | Hodge et al. | |
| 7,681,867 B2 | 3/2010 | Hu et al. | |
| 7,682,067 B2 | 3/2010 | West et al. | |
| 7,879,599 B2 | 2/2011 | Goodwin | |
| 7,935,101 B2 | 5/2011 | Muramatsu | |
| 8,282,267 B2 | 10/2012 | Castillo et al. | |
| 8,485,727 B2 * | 7/2013 | Trouilly | A23L 33/17 206/219 |
| 8,603,805 B2 | 12/2013 | Goodwin et al. | |
| 8,960,486 B2 | 2/2015 | Goodwin | |
| 9,005,971 B2 | 4/2015 | Goodwin et al. | |
| 9,259,692 B2 | 2/2016 | Goodwin et al. | |
| 9,376,655 B2 | 6/2016 | Larsen et al. | |
| 9,643,133 B2 | 5/2017 | Goodwin et al. | |
| 2001/0031491 A1 | 10/2001 | Curtis | |
| 2002/0063347 A1 | 5/2002 | Lee et al. | |
| 2002/0131654 A1 | 9/2002 | Smith et al. | |
| 2003/0036192 A1 | 2/2003 | Singh | |
| 2003/0077466 A1 | 4/2003 | Smith et al. | |
| 2003/0119185 A1 | 6/2003 | Berenson et al. | |
| 2004/0058436 A1 | 3/2004 | Zhang et al. | |
| 2004/0062140 A1 | 4/2004 | Cadogan et al. | |
| 2004/0095842 A1 | 5/2004 | Weetman | |
| 2004/0134802 A1 | 7/2004 | Inoue | |
| 2004/0210288 A1 | 10/2004 | Karapetyan | |
| 2005/0032205 A1 | 2/2005 | Smith | |
| 2005/0158851 A1 | 7/2005 | Furey | |
| 2005/0218075 A1 | 10/2005 | Graetz et al. | |
| 2005/0239199 A1 | 10/2005 | Kunas et al. | |
| 2005/0242114 A1 | 11/2005 | Savage et al. | |
| 2005/0272146 A1 | 12/2005 | Hodge et al. | |
| 2005/0282269 A1 | 12/2005 | Proulx | |
| 2006/0054557 A1 | 3/2006 | Hori et al. | |
| 2006/0196501 A1 | 9/2006 | Bibbo et al. | |

(56) References Cited

U.S. PATENT DOCUMENTS

| | | | |
|---|---|---|---|
| 2006/0270036 A1* | 11/2006 | Goodwin | B01F 3/04269 435/395 |
| 2007/0037279 A1 | 2/2007 | Courtois et al. | |
| 2008/0068920 A1 | 3/2008 | Galliher et al. | |
| 2008/0139865 A1 | 6/2008 | Galliher et al. | |
| 2008/0293133 A1 | 11/2008 | Reid et al. | |
| 2009/0035856 A1 | 2/2009 | Galliher et al. | |
| 2009/0113753 A1 | 5/2009 | Pepper | |
| 2009/0140005 A1 | 6/2009 | Reichert et al. | |
| 2010/0072216 A1 | 3/2010 | Voute | |
| 2010/0078395 A1 | 4/2010 | Shevitz | |
| 2010/0174099 A1 | 7/2010 | Behkish | |
| 2010/0264100 A1 | 10/2010 | Rivera et al. | |
| 2011/0013473 A1 | 1/2011 | Ludwig et al. | |
| 2011/0014689 A1 | 1/2011 | Gandlur | |
| 2011/0020922 A1 | 1/2011 | Wuenn et al. | |
| 2011/0070648 A1 | 3/2011 | Anneren et al. | |
| 2012/0238011 A1 | 9/2012 | Tuohey et al. | |
| 2012/0313267 A1 | 12/2012 | Pradel et al. | |
| 2013/0158635 A1 | 6/2013 | Federico et al. | |
| 2015/0069072 A1 | 3/2015 | Kelley | |
| 2015/0118753 A1 | 4/2015 | Brau | |
| 2016/0244710 A1 | 8/2016 | Wood | |
| 2016/0304825 A1 | 10/2016 | Larsen et al. | |

FOREIGN PATENT DOCUMENTS

| | | |
|---|---|---|
| CN | 101696388 A | 4/2010 |
| CN | 101977673 A | 2/2011 |
| DE | 200 07 347 U1 | 8/2000 |
| DE | 202010013812 U1 | 2/2011 |
| EP | 0 343 885 A1 | 11/1989 |
| EP | 0725134 A2 | 7/1996 |
| EP | 1 602 715 A2 | 12/2005 |
| FR | 2 519 020 | 1/1983 |
| FR | 2 797 887 A1 | 3/2001 |
| FR | 2 799 138 | 4/2001 |
| GB | 2 202 549 A | 9/1988 |
| JP | S50-119561 | 9/1975 |
| JP | S58-224683 | 12/1983 |
| JP | S61-067476 | 4/1986 |
| JP | S62-160899 | 7/1987 |
| JP | H02-31825 | 2/1990 |
| JP | H02-283274 | 11/1990 |
| JP | H03-010675 | 1/1991 |
| JP | H03-242297 | 10/1991 |
| JP | H05-336957 | 12/1993 |
| JP | H06-153902 | 6/1994 |
| JP | H07-08264 | 1/1995 |
| JP | H07-155170 | 6/1995 |
| JP | H08-224076 | 9/1996 |
| JP | H10-099071 | 4/1998 |
| JP | S63-84483 | 4/1998 |
| JP | H10-150972 | 9/1998 |
| JP | H10-313718 | 12/1998 |
| JP | H11-502716 | 3/1999 |
| JP | H11-299478 | 11/1999 |
| JP | 2001-258547 | 9/2001 |
| JP | 2002-101867 | 4/2002 |
| JP | 2007-511230 | 5/2007 |
| JP | 2008-536685 A | 9/2008 |
| RU | 2 220 917 C1 | 1/2004 |
| WO | 92/15491 | 9/1992 |
| WO | 1996/30497 | 10/1996 |
| WO | 2001/25394 | 4/2001 |
| WO | 2002/41484 A2 | 5/2002 |
| WO | 2005/068059 A1 | 7/2005 |
| WO | 2005/118771 | 12/2005 |
| WO | 2006/116067 A1 | 11/2006 |
| WO | 2007/134267 A2 | 11/2007 |
| WO | 2008/040568 A1 | 4/2008 |
| WO | 2008/157181 A1 | 12/2008 |
| WO | 2009/115241 | 9/2009 |
| WO | 2009/153425 | 12/2009 |
| WO | 2011/025890 A1 | 3/2011 |
| WO | 2011/079165 A1 | 6/2011 |
| WO | 2012/158108 A1 | 11/2012 |
| WO | 2013/049692 A1 | 4/2013 |

* cited by examiner

BAG ASSEMBLY AND SYSTEM FOR USE WITH A FLUID

CROSS-REFERENCE TO RELATED APPLICATIONS

This application is a continuation of U.S. application Ser. No. 14/738,442, filed Jun. 12, 2015, which is a continuation of U.S. application Ser. No. 14/315,936, filed Jun. 26, 2014, U.S. Pat. No. 9,079,690, which are hereby incorporated by specific reference in their entirety.

FIELD OF THE INVENTION

The present invention is directed to a bag assembly and a bag system that can be used with a fluid. More particularly, the present invention is directed to a tufted bag assembly and a bag system that can be used with a fluid, such as for containing a fluid during freezing.

BACKGROUND OF THE INVENTION

Various liquids, such as culture media, buffers, reagents, bodily fluids, and other biological materials are used extensively in research and development. Often, the liquids include precise compositions with components which begin to degrade after collection or preparation. Due to the degradation of the components, many liquids have finite shelf-lives that limit availability and long-term storage. Additionally, relatively shorter shelf-lives may result in increased costs from increased production and shipping.

To increase shelf-life, the liquids may be frozen after collection or preparation. Typically, the liquids are collected, prepared, and/or frozen in pliable containers, such as bags. However, due to expansion and uneven freezing, a projection frequently forms on the frozen liquid. The projection creates difficulty in storing multiple containers, and may damage the bags, resulting in contamination, leakage, and/or loss of the liquids.

One method of reducing damage to the bags includes decreasing the volume of liquid within the bag prior to freezing. However, the decreased volume of liquid still includes an uneven distribution of liquid expansion during freezing, which may damage the bag and create difficulty in storing multiple containers. Furthermore, the decreased volume of liquid increases unused space within the container, which increases shipping cost.

A freezer bag, storage system, and method of freezing that show one or more improvements in comparison to the prior art would be desirable in the art.

BRIEF DESCRIPTION OF THE INVENTION

Exemplary embodiments are directed to freezer bags for increasing uniform freezing of fluids contained therein.

In one embodiment, a freezer bag includes a pliable housing including at least one panel and a seam, the at least one panel and the seam defining a cavity within the pliable housing, a port extending from the pliable housing, and a tufting coupling opposing sides of the pliable housing, the tufting dividing the cavity into a plurality of regions.

In another embodiment, a storage system includes a freezer bag and a rigid container. The freezer bag comprises a pliable housing including at least one panel and a seam, the at least one panel and the seam defining a cavity within the pliable housing, a port extending from the pliable housing, and a tufting coupling opposing sides of the pliable housing, the tufting dividing the cavity into a plurality of regions. The rigid container comprises a first portion and a second portion, each portion comprising a dimpled section, a wall, and a plurality of feet. The rigid container is arranged and disposed to receive the freezer bag.

In another embodiment, a method of freezing includes providing a freezer bag comprising a pliable housing including at least one panel and a seam, the at least one panel and the seam defining a cavity within the pliable housing, a port extending from the pliable housing, and a tufting coupling opposing sides of the pliable housing, the tufting dividing the cavity into a plurality of regions; providing a fluid in the cavity, the fluid at least partially filling each of the regions; and freezing the fluid within the cavity of the freezer bag. The regions increase uniform freezing of the fluid.

An advantage of exemplary embodiments is that a tufting of the freezer bag forms regions for receiving fluid therein.

Another advantage of exemplary embodiments is an increase in uniform freezing of fluids contained within the freezer bag.

Yet another advantage of exemplary embodiments is a reduction or elimination of projections formed during freezing of fluids contained within the freezer bag.

Still another advantage of exemplary embodiments is that the reduction or elimination of projections facilitates stacking of the freezer bags.

Another advantage of exemplary embodiments is an ability to maintain freezer bag integrity during freezing.

Yet another advantage of exemplary embodiments is an ability to store freezer bags in a container without the energy of expansion separating and/or deforming the container during freezing.

Still another advantage of exemplary embodiments is an ability to freeze an increased volume of fluid without disturbing bag integrity by providing increased uniform freezing of the fluid.

Other features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Figure 1:
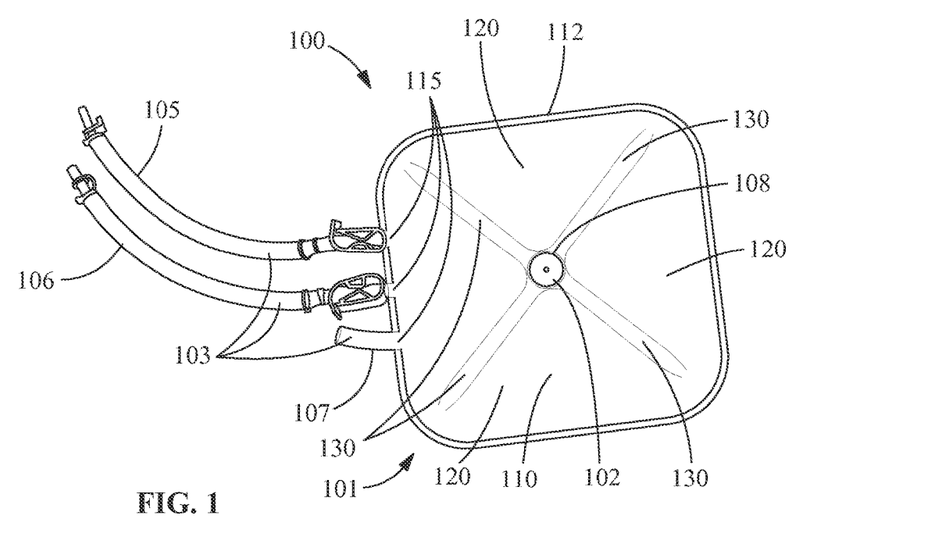
FIG. 1 is a perspective view of a freezer bag, according to an embodiment of the disclosure.

As illustrated in FIG. 1, a freezer bag 100 includes a pliable housing 101, a tufting 102, and one or more ports 103. The pliable housing 101 is formed from any suitable combination of panels 110 and/or seams 112. For example, in one embodiment the pliable housing 101 includes two panels 110a, 110b (FIG. 5) secured to each other along a seam 112 to define a cavity configured to receive and hold a fluid, such as a liquid, therein. In another embodiment, the pliable housing 101 includes one panel 110 folded over on itself and secured along the seam 112 to define the cavity. Other embodiments include a plurality of the panels 110 secured to each other along a plurality of seams 112 to define the cavity.

Each of the panels 110 comprises one or more plies of a flexible sheet or film-like material for providing pliability and support to the liquid contained within the cavity. The material includes any pliable, freeze resistant thermoplastic material and may include, by way of example only, ethylene vinyl acetate. Preferably, USP Class VI materials are employed that are capable of withstanding sterilization without degradation and which do not become brittle at temperatures of up to −70 C or lower.

The pliable housing 101 can be any shape and/or size as determined by the cavity formed therein. Suitable sizes of the pliable housing 101 include, but are not limited to, greater than about 50 L, between about 50 L and about 200 L, up to about 50 L, between about 100 mL and about 50 L, up to about 25 L, up to about 20 L, between about 100 mL and about 20 L, up to about 16 L, up to about 6 L, about 2 L, between about 100 mL and about 1 L, or any combination, sub-combination, range, or sub-range thereof. Suitable shapes of the pliable housing 101 and/or the cavity include, but are not limited to, spherical, semi-spherical, square, rounded square, rectangular, rounded rectangle, any other rounded or polygonal, or a combination thereof.

Figure 2:
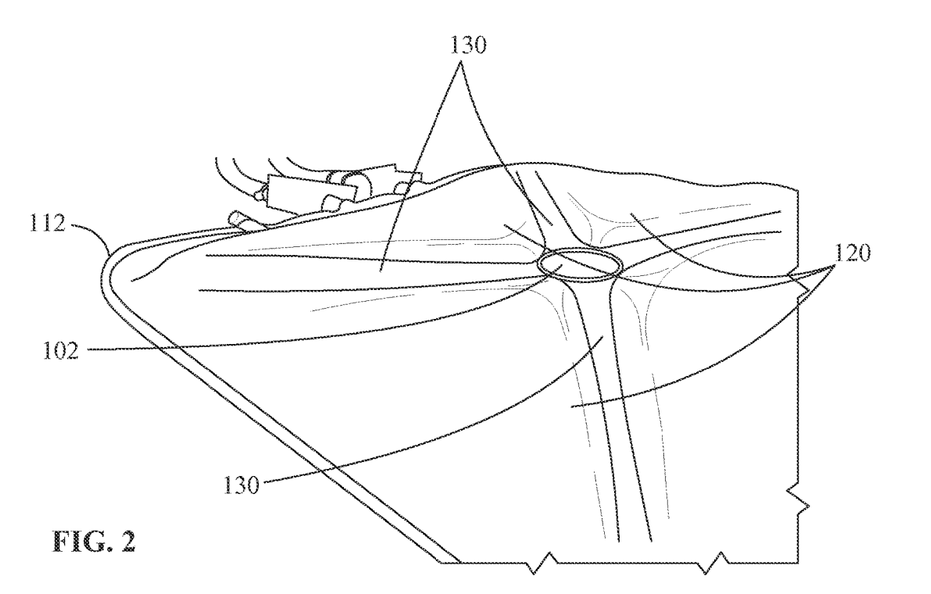
FIG. 2 is a perspective view of the freezer bag of FIG. 1 filled with fluid.

The tufting 102 couples opposing sides of the pliable housing 101 together. As illustrated in FIGS. 1-2, a single tufting 102 couples the two panels 110a, 110b together at a substantially central location within the cavity. In one embodiment, the panels 110 are secured directly to each other to form the tufting 102 by a circular seal 108. In another embodiment, the panels 110 are coupled through a tufting member, such as, but not limited to, a circular or saucer shaped disk. The tufting 102 may be formed by any sealing technique, such as, but not limited to, heat sealing, radio frequency (RF) sealing, induction sealing, any other film sealing technique, or a combination thereof. The tufting 102 reduces or eliminates movement of the panels 110 relative to each other and reduces or eliminates separation of the panels 110 at the tufting, i.e. in the center of the cavity as shown in FIGS. 1 and 2. The seam 112 and the centrally located tufting 102 define a toroid shaped cavity (e.g., torus, doughnut, ring) for receiving a fluid.

To fill the cavity with fluid, a fluid source is connected to the port 103. The port 103 is coupled to a break 115 in the seam 112, the port 103 and the break 115 together providing access to the cavity within the pliable housing 101. In one embodiment, the port 103 provides a sterile inlet to and/or outlet from the cavity within the pliable housing 101. As shown in FIGS. 1-4, the freezer bag 100 includes a plurality of ports 103. For example, the plurality of ports 103 may include a male port 105, a female port 106, and/or an injection port 107. Each of the ports 103 may be used to provide fluid to, or remove fluid from, the cavity within the pliable housing 101. Each of the ports 103 may additionally include a cap, a clamp, and/or any other feature to facilitate coupling of the port 103 and/or control of fluid flow into, or out of, the pliable housing 101.

The tufting 102 effectively divides the cavity into separate regions 120 of fluid as the cavity is filled. Filling the pliable housing 101 with fluid expands the cavity, which separates portions of the panels 110 not coupled by the tufting 102 or along the edge at the seam 112. As the portions of the panels 110 separate, the tufting 102 forms a depression in the pliable housing 101. The depression formed by the tufting 102 generates recesses 130 in the panels 110, the recesses 130 defining the regions 120. The regions 120 are in fluid communication with each other to facilitate the flow of fluid between the regions 120 and allowing a generally equal distribution of fluid about the bag. However, the regions 120 provide identifiable segments of fluid having reduced volume as compared to the entire volume of liquid within the cavity.

Figure 3:
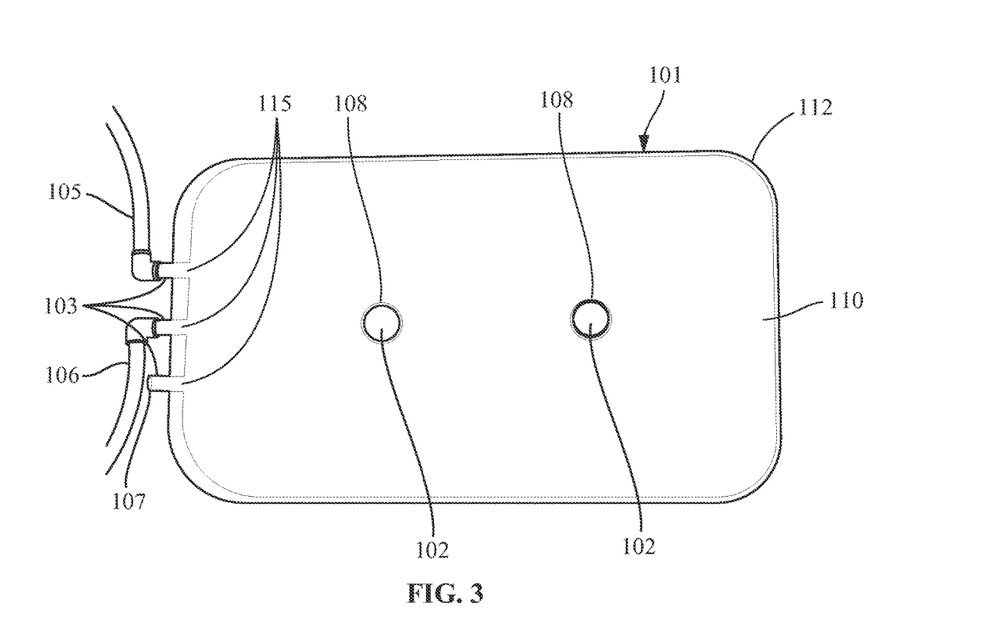
FIG. 3 is a perspective view of a freezer bag, according to an embodiment of the disclosure.
Figure 4:
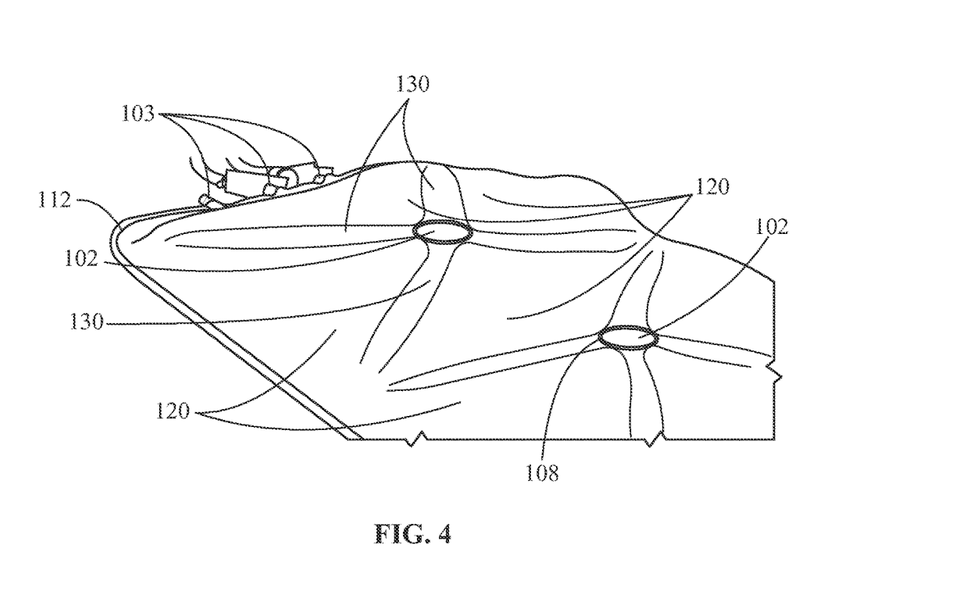
FIG. 4 is a perspective view of the freezer bag of FIG. 3 filled with fluid.

It will be appreciated that in some embodiments, the pliable housing 101 includes more than one tufting 102. For example, as illustrated in FIGS. 3-4, the freezer bag 100 includes at least two of tuftings 102 positioned centrally along a length of the pliable housing 101. Increasing the number of tuftings 102 increases the number of regions 120 formed in the pliable housing 101. Additionally, based upon a positioning of the tuftings 102, increasing the number of regions 120 decreases the size of each region 120.

Figure 5:
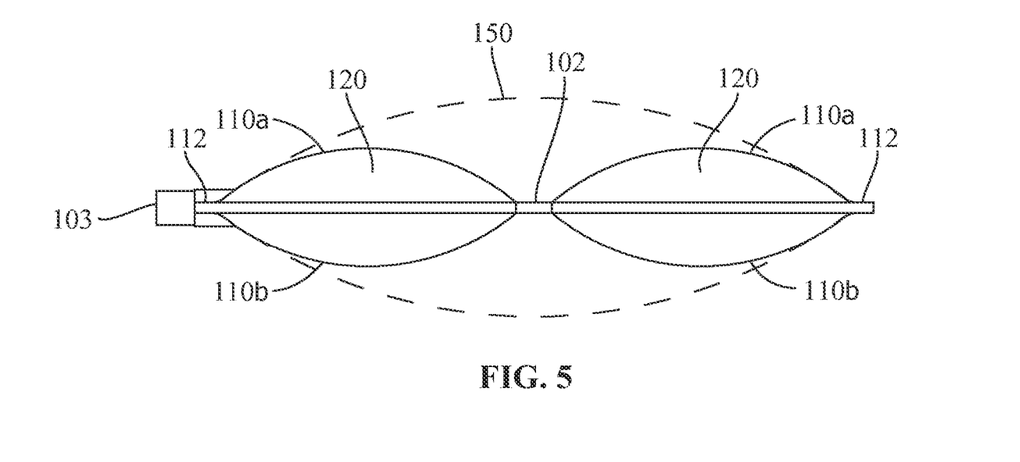
FIG. 5 is a section view of a freezer bag and a conventional bag.

Turning to FIG. 5, schematically illustrated is a cross-sectional view of a filled bag having a single tufting in accordance with the embodiment shown in FIGS. 1 and 2 juxtaposed with a conventional bag 150 shown in dotted line for purposes of comparison. The single tufting is positioned in a location where, without the tufting, the conventional bag 150 would include the largest amount of expansion, i.e., the thickest section of the conventional bag 150 when filled. The fluid in the thickest section is the last to freeze, and where projections from a concentration of fluid expansion would be most likely to occur. The tufting 102 positioned in the thickest section, such as, for example, a central portion of the conventional bag 150, prevents the thickest section from fully expanding and forms multiple regions 120 having a comparatively smaller thickness than the conventional bag 150.

The decreased thickness of each region 120 decreases the thickness of the fluid at any one point in the freezer bag 100, and thus, decreases the freezer bag 100's ability to form a large "belly". Additionally, the tufting 102 distributes fluid between the regions 120 around the tufting 102 for a more uniform fluid thickness compared to the conventional bag 150 which expands significantly at the center to form the belly, despite both containing the same amount of fluid. Together, the decreased thickness at any one point and the increased uniformity of thickness throughout the freezer bag 100 provide a more uniform freezing of the fluid to decrease or eliminate the formation of projections. By decreasing or eliminating the formation of projections, the tufting 102 can both decrease damage to the freezer bag 100 and increase its stackability. It will be appreciated that the fill volume of the bag, i.e., the volume of the bag which is filled with fluid, is something less than the total volume of the bag in order to accommodate liquid expansion during freezing. By decreasing or eliminating the formation of projections, the tufting permits an increase in the fill volume of the bag.

The freezer bag 100 may be exposed to a temperature of at −70° C. or lower to freeze the fluid. The decreased thickness of the fluid in each of the regions 120 increases uniform freezing of the fluid as compared to the conventional bag 150 having the belly with increased thickness, the central portions of which would take comparatively longer to freeze and decreasing projection (sometime also referred to as cyst or tumor) formation of the liquid that can result during when uneven freezing occurs, particularly as areas in the thickest central portion of the bag remain liquid while the areas around it already have frozen. Additionally, the regions 120 distribute the expansion of the liquid throughout the cavity to reduce the total expansion in any one portion of the freezer bag 100.

In one embodiment, the number of tuftings 102 secured to the panels 110 is selected based upon a size of the pliable housing 101 and/or a number of regions 120 to be formed in the pliable housing 101. For example, a 6 L pliable housing 101 may have a single tufting 102, while a larger pliable housing 101, such as a 16 L pliable housing 101, may include 3-4 of the tuftings 102 to provide an increased number of regions 120. Additionally, a size of each of the tuftings 102 may be varied, such as, for example, between pliable housings 101 having different sizes. Varying the size of the tufting varies the size of each region 120, varies the configuration of the regions 120, varies the strength of the tufting 102, or a combination thereof. Increasing the number of regions 120 and/or decreasing the size of each region 120 decreases a thickness of the region 120 when filled with liquid. The decreased thickness of the liquid in the region 120 further increases uniform freezing of the liquid and distribution of liquid expansion throughout the cavity.

The increase in uniform freezing and/or the decreased expansion of liquid in any one portion of the cavity reduces the size and/or formation of projections that may damage the pliable housing 101. In one embodiment, reducing the size and/or formation of projections facilitates filling the freezer bag 100 with an increased volume of fluid prior to freezing. In a further embodiment, the unfilled volume in the freezer bag 100 provides room for the expansion of the fluid during freezing, while the reduced size and/or formation of projections reduces stress applied by the projections at any one point of the pliable housing 101. The reduced size and/or formation of the projections also facilitates stacking and/or storage of the freezer bag 100 by forming an exterior surface substantially devoid of projections.

Figure 6:
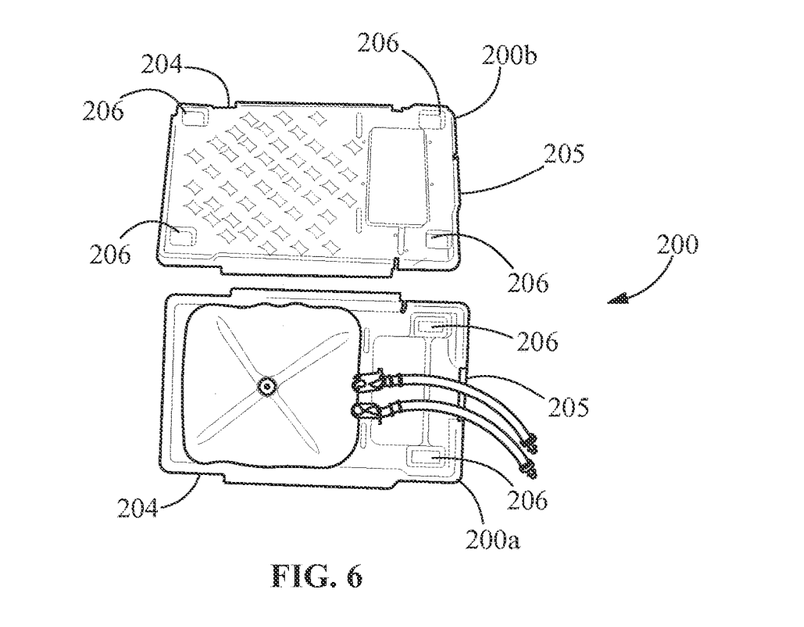
FIG. 6 is a perspective view of a container for housing the freezer bag of FIG. 1.
Figure 7:
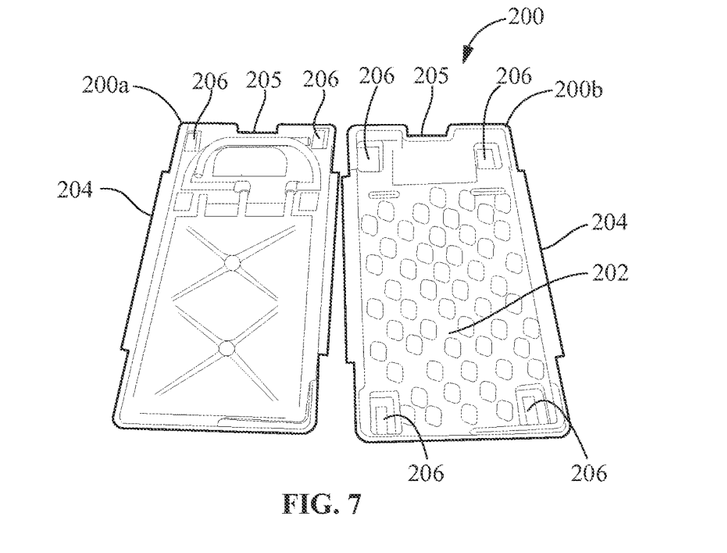
FIG. 7 is a perspective view of a container for housing the freezer bag of FIG. 3.
Figure 8:
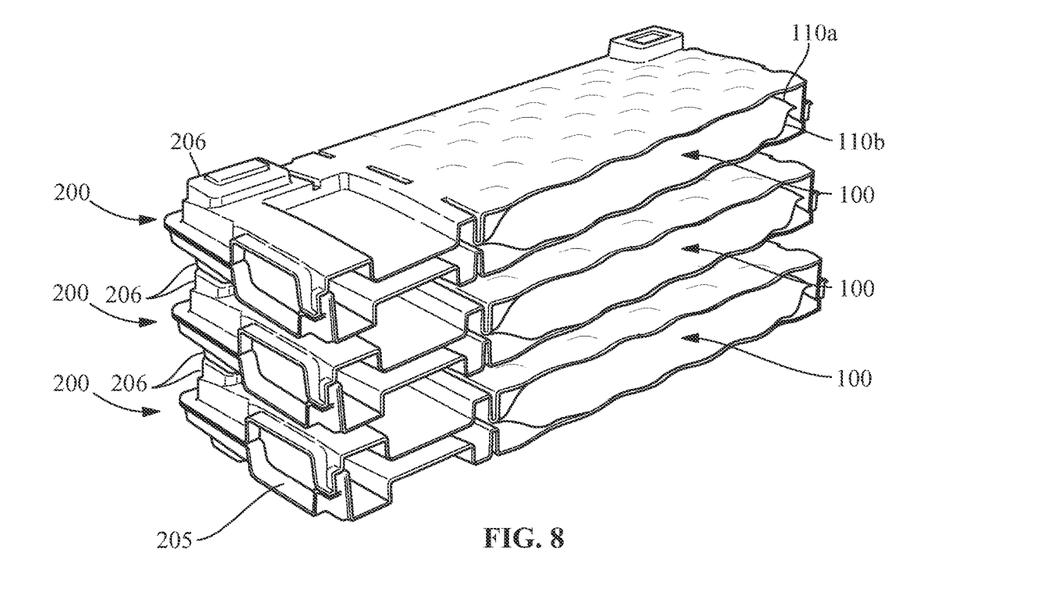
FIG. 8 is a partial cross-sectional perspective view of a stack of the containers of FIG. 6 in their closed position.

To further facilitate stacking and/or storage of the freezer bag 100, a storage system may include the freezer bag 100 and a container 200. As illustrated in FIGS. 6-8, the container 200 includes two portions 200a and 200b. In one embodiment, the two portions 200a, 200b are mirror images of each other. In another embodiment, each portion 200a, 200b includes a dimpled section 202, a wall 204, and a plurality of feet 206. The two portions 200a, 200b may be pivotably and/or detachably secured to each other, include corresponding mating features, or a combination thereof. To close the container 200, the portions 200a, 200b are positioned opposite each other such that the walls 204 of the portions 200a, 200b are adjacent and/or in contact with each other. In a further embodiment, the corresponding mating features include extending and/or receiving portions along the wall 204 to orient and/or secure the portions 200a, 200b together. The container 200 may also include a securing member, such as, but not limited to, a clasp, fastener, or other device to secure the portions 200a, 200b in a closed position.

Prior to closing the container 200, the freezer bag 100 is positioned on the dimpled section 202 of either portion 200a, 200b. In one embodiment, the portions 200a, 200b are then closed to secure the freezer bag 100 between the dimpled sections 202. The dimpled sections 202 interlock the freezer bag 100 with the container 200 when the freezer bag 100 is in a frozen state. In another embodiment, each of the sections 200a, 200b includes a gap 205 in the wall 204.

When the container 200 is closed, the gaps 205 form an opening to facilitate passage of the at least one port 103 therethrough. The closed container 200 including the freezer bag 100 is then positioned in a freezer to freeze the fluid within the freezer bag 100.

In one embodiment, stacking the containers 200 includes positioning the feet 206 of one container 200 on or adjacent to the feet 206 of another container 200. In another embodiment, the plurality of feet 206 includes alternating mating features that facilitate stacking and orienting multiple containers 200 on top of each other. As illustrated in FIGS. 6-8, the container 200 includes four feet 206, two of the feet 206 including a raised rectangular portion, and two of the feet 206 including a recessed rectangular portion. The raised rectangular portions on the feet 206 of one container 200 are positioned within the recessed rectangular portions on the feet 206 of another container 200 to reduce or eliminate movement of the containers 200 relative to each other when stacked.

In a further embodiment, the feet 206 facilitate uniform freezing of the freezer bags 100 by providing an open space for cold air to flow between the stacked containers 200. The uniform freezing of the fluid reduces or eliminates the formation of projections during freezing, which reduces or eliminates pressure applied to the container 200 by the projections. By reducing or eliminating the pressure applied to the container 200, the uniform freezing decreases deformation of container 200, separation of the portions 200a, 200b, and/or damage to the freezer bag 100 from the projections.

Each of portions 200a and 200b comprise an example of a support structure having a front face with a plurality of recesses (dimpled sections 202) formed thereon. During use, freezer bags 100 are disposed on the front face of the support structure so as to cover at least a portion of each of the plurality of recesses.

While the invention has been described with reference to one or more embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A bag assembly, comprising: a pliable housing comprising a first panel secured to a second panel by a seam so that a cavity is formed between the first panel and the second panel, the seam encircling the cavity, the cavity being configured to receive and hold a fluid; a first tufting coupling together the first panel and the second panel at a location spaced apart from the seam so that the cavity encircles the first tufting, the first tufting being circular; and a first port coupled with the pliable housing and communicating with the cavity.

2. The bag assembly of claim 1, wherein the first panel comprises a flexible film.

3. The bag assembly of claim 2, wherein the second panel comprises a flexible film.

4. The bag assembly of claim 1, wherein the first panel is square, rounded square, rectangular, or rounded rectangular.

5. The bag assembly of claim 1, wherein the first tufting comprises a heat seal, a radio frequency seal or an induction seal between the first panel and the second panel.

6. The bag assembly of claim 1, wherein the cavity has a toroid shape.

7. The bag assembly of claim 1, further comprising a liquid fluid source coupled to the first port.

8. The bag assembly of claim 1, wherein the first tufting couples together the first panel and the second panel at a central location within the cavity.

9. The bag assembly of claim 1, further comprising a second tufting coupling together the first panel and the second panel at a location spaced apart from the seam and spaced apart from the first tufting so that the cavity encircles the second tufting.

10. The bag assembly of claim 9, wherein the second tufting is circular.

11. The bag assembly of claim 9, wherein the first tufting and the second tufting are different sizes.

12. The bag assembly of claim 1, further comprising a second port coupled with the pliable housing.

13. A bag system comprising:
the bag assembly as recited in claim 1; and
a support structure having a front face with a plurality of recesses formed thereon, the bag assembly being disposed on the front face of the support structure so as to cover at least a portion of each of the plurality of recesses.

14. A bag assembly, comprising: a pliable housing comprising a first panel secured to a second panel by a seam so that a cavity is formed between the first panel and the second panel, the seam encircling the cavity, the cavity being configured to receive and hold a fluid; a first tufting coupling together the first panel and the second panel at a location spaced apart from the seam so that the cavity encircles the first tufting; a second tufting coupling together the first panel and the second panel at a location spaced apart from the seam and spaced apart from the first tufting so that the cavity encircles the second tufting; and a first port coupled with the pliable housing and communicating with the cavity.

15. The bag assembly of claim 14, wherein at least the first tufting or the second tufting is circular.

16. The bag assembly of claim 14, wherein at least the first panel or the second panel comprises a flexible film.

17. The bag assembly of claim 14, wherein the first tufting and the second tufting are different sizes.

18. The bag assembly of claim 14, further comprising a second port coupled with the pliable housing.

19. A bag system comprising:
the bag assembly as recited in claim 14; and
a support structure having a front face with a plurality of recesses formed thereon, the bag assembly being disposed on the front face of the support structure so as to cover at least a portion of each of the plurality of recesses.

20. A bag system, comprising:
a bag assembly comprising:
a pliable housing comprising a first panel secured to a second panel by a seam so that a cavity is formed between the first panel and the second panel, the seam encircling the cavity;
a first tufting coupling together the first panel and the second panel at a location spaced apart from the seam so that the cavity encircles the first tufting; and
a first port coupled with the pliable housing and communicating with the cavity; and
a support structure having a front face with a plurality of recesses formed thereon, the bag assembly being disposed on the front face of the support structure so as to cover at least a portion of each of the plurality of recesses.

* * * * *